(12) United States Patent
Cormier et al.

(10) Patent No.: US 7,963,935 B2
(45) Date of Patent: Jun. 21, 2011

(54) MICROPROJECTION ARRAY HAVING A BENEFICIAL AGENT CONTAINING COATING

(75) Inventors: Michel J. N. Cormier, Mountain View, CA (US); Wendy A. Young, San Jose, CA (US); Juanita A. Johnson, Belmont, CA (US); Peter E. Daddona, Menlo Park, CA (US)

(73) Assignee: Alza Corporation, Vacaville, CA (US)

( * ) Notice: Subject to any disclaimer, the term of this patent is extended or adjusted under 35 U.S.C. 154(b) by 1859 days.

(21) Appl. No.: 10/127,108

(22) Filed: Apr. 20, 2002

(65) Prior Publication Data

US 2002/0177839 A1 Nov. 28, 2002

Related U.S. Application Data

(60) Provisional application No. 60/285,576, filed on Apr. 20, 2001.

(51) Int. Cl.
*A61B 17/20* (2006.01)
(52) U.S. Cl. ........................................ 604/46
(58) Field of Classification Search ............ 604/46, 604/116, 171; 424/422–424; 427/2.1
See application file for complete search history.

(56) References Cited

U.S. PATENT DOCUMENTS

| | | | |
|---|---|---|---|
| 3,136,314 A | 6/1964 | Kravitz | |
| RE25,637 E | 9/1964 | Kravitz et al. | |
| 3,556,080 A * | 1/1971 | Hein | 600/556 |
| 3,760,984 A * | 9/1973 | Theeuwes | 222/95 |
| 3,814,097 A | 6/1974 | Ganderton et al. | |
| 3,964,482 A | 6/1976 | Gerstel et al. | |
| 4,109,655 A | 8/1978 | Chacornac | |
| 4,453,926 A | 6/1984 | Galy | |
| 4,473,083 A * | 9/1984 | Maganias | 600/556 |
| 5,066,494 A | 11/1991 | Becher | |
| 5,250,023 A * | 10/1993 | Lee et al. | 604/20 |
| 5,279,544 A | 1/1994 | Gross et al. | |
| 5,457,041 A * | 10/1995 | Ginaven et al. | 435/455 |
| 5,738,728 A | 4/1998 | Tisone | |
| 5,741,554 A | 4/1998 | Tisone | |
| 5,743,960 A | 4/1998 | Tisone | |
| 5,770,220 A | 6/1998 | Meconi et al. | |
| 5,847,726 A | 12/1998 | Hori | |
| 5,879,326 A | 3/1999 | Godshall et al. | |

(Continued)

FOREIGN PATENT DOCUMENTS

CN 1193916 9/1998

(Continued)

OTHER PUBLICATIONS

U.S. Appl. No. 60/276,762, J. Trautman et al.

(Continued)

*Primary Examiner* — Nicholas D Lucchesi
*Assistant Examiner* — Victoria P Campbell
(74) *Attorney, Agent, or Firm* — Edwards Angell Palmer & Dodge LLP; Kathleen Williams; Amy DeCloux

(57) ABSTRACT

The device including a plurality of stratum corneum-piercing microprojections, and a solid coating disposed upon the microprojections, wherein the solid coating includes at least one beneficial agent and a biocompatible carrier is provided. The device is applied to the skin of a living animal (e.g., a human), causing the microprojections to pierce the stratum corneum and deliver an effective dose of the agent to the animal.

11 Claims, 2 Drawing Sheets

U.S. PATENT DOCUMENTS

| | | | |
|---|---|---|---|
| 5,916,524 A | 6/1999 | Tisone | |
| 5,983,136 A | 11/1999 | Kamen | |
| 6,050,988 A * | 4/2000 | Zuck | 604/890.1 |
| 6,083,196 A * | 7/2000 | Trautman et al. | 604/46 |
| 6,091,975 A | 7/2000 | Daddona et al. | |
| 6,136,343 A | 10/2000 | Baichwal et al. | |
| 6,197,013 B1 * | 3/2001 | Reed et al. | 604/509 |
| 6,219,574 B1 * | 4/2001 | Cormier et al. | 604/20 |
| 6,230,051 B1 | 5/2001 | Cormier et al. | |
| 6,290,991 B1 * | 9/2001 | Roser et al. | 424/502 |
| 6,322,808 B1 | 11/2001 | Trautman et al. | |
| 6,331,310 B1 | 12/2001 | Roser et al. | |
| 6,334,856 B1 * | 1/2002 | Allen et al. | 604/191 |
| 6,379,324 B1 | 4/2002 | Gartstein et al. | |
| 6,440,096 B1 | 8/2002 | Lastovich et al. | |
| 6,451,240 B1 * | 9/2002 | Sherman et al. | 264/504 |
| 6,454,755 B1 | 9/2002 | Godshall | |
| 6,503,231 B1 * | 1/2003 | Prausnitz et al. | 604/272 |
| 6,537,242 B1 | 3/2003 | Palmer | |
| 6,558,361 B1 * | 5/2003 | Yeshurun | 604/272 |
| 6,565,532 B1 | 5/2003 | Yuzhakov et al. | |
| 6,589,202 B1 | 7/2003 | Powell | |
| 6,623,457 B1 * | 9/2003 | Rosenberg | 604/191 |
| 6,638,246 B1 * | 10/2003 | Naimark et al. | 604/103 |
| 6,652,478 B1 | 11/2003 | Gartstein et al. | |
| 6,689,100 B2 | 2/2004 | Connelly et al. | |
| 6,692,456 B1 * | 2/2004 | Eppstein et al. | 604/22 |
| 6,743,211 B1 | 6/2004 | Prausnitz et al. | |
| 6,811,792 B2 | 11/2004 | Roser et al. | |
| 6,835,184 B1 | 12/2004 | Sage et al. | |
| 6,855,131 B2 | 2/2005 | Trautman et al. | |
| 6,855,372 B2 | 2/2005 | Trautman et al. | |
| 6,881,203 B2 | 4/2005 | Delmore | |
| 6,884,427 B1 | 4/2005 | Barrows | |
| 6,918,901 B1 | 7/2005 | Theeuwes et al. | |
| 6,931,277 B1 | 8/2005 | Yuzhakov et al. | |
| 6,953,589 B1 | 10/2005 | Trautman et al. | |
| 7,131,960 B2 | 11/2006 | Trautman et al. | |
| 7,184,826 B2 | 2/2007 | Cormier et al. | |
| 2001/0038858 A1 * | 11/2001 | Roser et al. | 424/488 |
| 2002/0009464 A1 * | 1/2002 | Colaco | 424/204.1 |
| 2002/0016562 A1 * | 2/2002 | Cormier et al. | 604/20 |
| 2002/0082543 A1 | 6/2002 | Park et al. | |
| 2002/0087182 A1 | 7/2002 | Trautman et al. | |
| 2002/0128599 A1 | 9/2002 | Cormier et al. | |
| 2003/0100885 A1 | 5/2003 | Pettis et al. | |
| 2003/0135201 A1 | 7/2003 | Gonnelli | |
| 2003/0199811 A1 | 10/2003 | Sage, Jr. et al. | |
| 2005/0008683 A1 | 1/2005 | Mikszta et al. | |
| 2006/0047243 A1 | 3/2006 | Rosenberg | |
| 2006/0074377 A1 | 4/2006 | Cormier et al. | |

FOREIGN PATENT DOCUMENTS

| | | |
|---|---|---|
| EP | 0407063 A1 | 9/1991 |
| EP | 0844004 | 5/1998 |
| WO | WO 93/17754 | 9/1993 |
| WO | WO 96/17648 | 6/1996 |
| WO | WO 96/37155 | 11/1996 |
| WO | WO 96/37256 | 11/1996 |
| WO | WO 97/03718 | 2/1997 |
| WO | WO 97/48440 | 12/1997 |
| WO | WO 97/48441 | 12/1997 |
| WO | WO 97/48442 | 12/1997 |
| WO | WO 98/00193 | 1/1998 |
| WO | WO 98/11937 | 3/1998 |
| WO | WO 98/28037 | 7/1998 |
| WO | WO 98/29298 | 7/1998 |
| WO | WO 98/29365 | 7/1998 |
| WO | WO 99/64580 | 12/1999 |
| WO | WO 00/62759 | 10/2000 |
| WO | WO 01/56646 | 8/2001 |
| WO | WO 01/93931 | 12/2001 |
| WO | WO 02/07813 | 1/2002 |

OTHER PUBLICATIONS

U.S. Appl. No. 60/240,307, J. Trautman et al.
U.S. Appl. No. 60/240,436, J. Trautman et al.
International Search Report dated Aug. 6, 2002 for corresponding Appl. No. PCT/US 02/12730.

* cited by examiner

MICROPROJECTION ARRAY HAVING A BENEFICIAL AGENT CONTAINING COATING

This application claims priority from U.S. Provisional Patent Application Ser. No. 60/285,576 filed Apr. 20, 2001.

TECHNICAL FIELD

The present invention relates to administering and enhancing transdermal delivery of an agent across the skin. More particularly, the invention relates to a drug delivery system for administering a biologically active agent through the stratum corneum using skin-piercing microprojections, which have a substantially dry coating disposed thereupon, wherein a beneficial agent is contained within the coating. The microprojections pierce the skin to only a very shallow depth, preferably too shallow to reach blood carrying capillaries. Delivery of the agent is accomplished when the microprojections pierce the outermost layer(s) of the skin of a patient and release the active agent contained in the coating into the patient's skin tissue.

BACKGROUND ART

Drugs are most conventionally administered either orally or by injection. Unfortunately, many medicaments are completely ineffective or of radically reduced efficiency when orally administered since they either are not absorbed or are adversely affected before entering the blood stream and thus do not possess the desired activity. Transdermal delivery when compared to oral delivery avoids the harsh environments of the digestive tract, bypasses gastrointestinal drug metabolism, reduces first-pass effects, and avoids the possible deactivation by digestive and liver enzymes. Conversely, the digestive tract is not subjected to the drug during transdermal administration. On the other hand, the direct injection of the medicament into the bloodstream, while assuring no modification of the medicament in administration, is a difficult, inconvenient, painful and uncomfortable procedure, sometimes resulting in poor patient compliance. This is particularly true for vaccination of children, where the vaccinations must be delivered intramuscularly in a series of injections.

Hence, in principal, transdermal delivery provides for a method of administering drugs that would otherwise need to be delivered via hypodermic injection or intravenous infusion.

The word "transdermal" is used herein to mean the delivery of an agent (e.g., a therapeutic agent such as a drug) into or through the skin for local or systemic therapy. Transdermal agent delivery includes delivery via passive diffusion as well as by other external energy sources including electricity (e.g., iontophoresis) and ultrasound (e.g. phonophoresis). While drugs do diffuse across both the stratum corneum and the epidermis, the rate of diffusion through the intact stratum corneum is often the limiting step. Many compounds require higher delivery rates than can be achieved by simple passive transdermal diffusion. When compared to injections, transdermal agent delivery eliminates the associated pain and reduces the possibility of infection. Theoretically, the transdermal route of agent administration could be advantageous in the delivery of many therapeutic proteins, because proteins are susceptible to gastrointestinal degradation and exhibit poor gastrointestinal uptake. Additionally transdermal devices are more acceptable to patients than injections. However, the transdermal flux of medically useful peptides and proteins is often insufficient to be therapeutically effective due to the large size/molecular weight of these molecules. Often the delivery rate or flux is insufficient to produce the desired effect or the agent is degraded prior to reaching the target sight, for example the patient's blood stream.

Passive transdermal drug delivery systems generally rely on passive diffusion to administer the drug while active transdermal drug delivery systems rely on an external energy source (e.g., electricity) to deliver the drug. Passive transdermal drug delivery systems are more common. Passive transdermal systems have a drug reservoir containing a high concentration of drug adapted to contact the skin where the drug diffuses through the skin and into the body tissues or bloodstream of the patient. The transdermal drug flux is dependent upon the condition of the skin, the size and physical/chemical properties of the drug molecule, and the concentration gradient across the skin. Because of the low skin permeability to many drugs, transdermal delivery has had limited applications. This low permeability is attributed primarily to the stratum corneum, the outermost skin layer which consists of flat, dead cells filled with keratin fibers (keratinocytes) surrounded by lipid bilayers. The highly ordered structure of the lipid bilayers confers a relatively impermeable character to the stratum corneum.

One common method of increasing the passive transdermal diffusional drug flux, involves pre-treating the skin with, or co-delivering with the drug, a skin permeation enhancer. A permeation enhancer, when applied to a body surface through which the drug is delivered, enhances the flow of the drug therethrough. However, the efficacy of these methods in enhancing transdermal protein transport has been limited, at least for the larger proteins, due to their size. Active transport systems use an external energy source to assist the drug flux through the stratum corneum. One such enhancement for transdermal drug delivery is referred to as "electrotransport." This mechanism uses an electrical potential, which results in the application of electric current to aid in the transport of the agent through the body surface, such as skin. Other active transport systems use ultrasound (phonophoresis) or heat as the external energy source.

There also have been many attempts to mechanically penetrate or disrupt the outermost skin layers, thereby creating pathways into the skin in order to enhance the amount of agent being transdermally delivered. Early vaccination devices known as scarifiers generally had a plurality of tines or needles, which are applied to the skin to scratch or make small cuts in the area of application. The vaccine was applied either topically on the skin, such as described in U.S. Pat. No. 5,847,726 issued to Rabenau, or alternatively, as a wetted liquid that may be applied to the tines of the scarifier as shown and described in U.S. Pat. No. 4,453,926, issued to Galy; or U.S. Pat. No. 4,109,655 issued to Charcornac, or U.S. Pat. No. 3,136,314 issued to Kravitz. Scarifiers have been suggested for intradermal vaccine delivery in part because only very small amounts of the vaccine need to be delivered into the skin to be effective in immunizing the patient. Further, the amount of vaccine delivered is not particularly critical since a minimum amount achieves satisfactory immunization as well as an excess amount. However, a serious disadvantage in using a scarifier to deliver a drug is the difficulty in determining the transdermal drug flux and the resulting dosage delivered because it cannot be determined if the minimum amount was delivered. For example, in many instances, the agent disposed upon the skin piercing tines of an intradermal vaccination device is pushed off the tines during skin piercing. Further, many beneficial agents do not have good adhesion characteristics, after being coated onto tines or other skin piercing microprojections, so that the beneficial agent is easily dislodged from the surface of the microprojections. For example, a portion of the beneficial agent may be dislodged from the microprojections during use and not delivered to the patient, resulting in a situation where the patient may not receive the full dosage needed or required. Also, due to the elastic, resilient, and deforming nature of skin that allows it to deflect and resist puncturing, the tiny piercing elements often do not uniformly penetrate the skin and/or are wiped free of a liquid coating of an agent upon skin penetration. Additionally, due to the self healing process of the skin, the punctures or slits made in the skin tended to close up after removal of the piercing elements from the stratum corneum. Thus, the skin acts to remove active agent coating the tiny piercing elements upon penetration. Furthermore, the tiny slits formed by the piercing elements heal quickly after removal of the device, thus, limiting the passage of the agent through the passageways created by the piercing elements and in turn limiting the transdermal flux of such devices.

Other devices that use tiny skin piercing elements to enhance transdermal drug delivery are disclosed in European Patent 0407063A1; U.S. Pat. No. 5,879,326 issued to Godshall et al.; U.S. Pat. No. 3,814,097 issued to Ganderton et al.; U.S. Pat. No. 5,279,544 issued to Gross et al.; U.S. Pat. No. 5,250,023 issued to Lee et al.; U.S. Pat. No. 3,964,482 issued to Gerstel et al.; U.S. Pat. No. Reissue 25,637 issued to Kravitz et al.; and PCT Publications No. WO 96/37155, WO 96/37256, WO 96/17648, WO 97/03718, WO 98/11937, WO 98/00193, WO 97/48440, WO 97/48441, WO 97/48442, WO 98/00193, WO 99/64580, WO 98/28037, WO 98/29298, and WO 98/29365; all incorporated by reference in their entirety. These devices use piercing elements of various shapes and sizes to pierce the outermost layer (i.e. the stratum corneum) of the skin. The piercing elements disclosed in these references generally extend perpendicularly from a thin, flat member, such as a pad or sheet. The piercing elements in some of these devices are extremely small, some having dimensions (i.e., microblade length and width) of only about 25-400 micro-meters and a microblade thickness of only about 5-30 micro-meters. These tiny piercing/cutting elements make correspondingly small microslits in the stratum corneum for enhanced transdermal agent delivery therethrough.

Generally these systems include a reservoir for holding the drug and also a delivery system to transfer the drug from the reservoir through the stratum corneum, such as by hollow tines of the device itself. One example of such a device is disclosed in WO 93/17754, which has a liquid drug reservoir. The reservoir must be pressurized to force the liquid drug through the tiny tubular elements and into the skin. Disadvantages of devices such as these include the added complication and expense of adding a pressurizeable liquid reservoir and complications due to the presence of a pressure-driven delivery system. Another disadvantage of these systems is that they have a limited shelf life due to degradation of the beneficial agent within the liquid reservoir.

DISCLOSURE OF THE INVENTION

The device and method of the present invention overcome these limitations by transdermally delivering a biologically active agent using a microprojection array including a plurality of microprojections, which are coated with a solid substantially dry coating containing a beneficial agent therein. The present invention is directed to a device and method for delivering a beneficial agent, which may be a pharmacologically active agent through the stratum corneum, of preferably, a mammal and most preferable a human, by coating a plurality of stratum corneum piercing microprojections with an amorphous glassy coating that protects the beneficial agent prior to deployment in the stratum corneum. The beneficial agent is selected to be sufficiently potent to be effective when delivered from a solid coating on a plurality of skin piercing microprojections. The coating preferably has sufficient water solubility such that when the microprojections are disposed within the patient's tissue the coating is easily and quickly dissolved, thereby releasing the beneficial agent. Further, the coating is sufficiently adhered to the surfaces of the microprojections so that the coating is not dislodged from the microprojections during insertion of the array into the patient's tissue.

A preferred embodiment of this invention consists of a device for delivering a beneficial agent through the stratum corneum, the device including a plurality of stratum corneum-piercing microprojections; and a solid coating disposed upon the microprojections, wherein the solid coating includes at least one beneficial agent and a biocompatible carrier.

In another preferred embodiment of this invention, there is provided a device for forming a plurality of microslits through the stratum corneum for delivering a beneficial agent therethrough, the device including a plurality of microprojections extending from a substrate, the microprojections being sized and arranged to pierce human skin to a depth of less than about 500 micrometers, and a solid coating disposed upon the microprojections, wherein the solid coating includes a beneficial agent and a biocompatible carrier.

In another preferred embodiment of this invention there is provided a device for forming a plurality of microslits through the stratum corneum for delivering a beneficial agent therethrough, the device including a plurality of microprojections extending from a substrate, the microprojections being sized and arranged to pierce human skin to a depth of less than about 500 micrometers, and a solid coating disposed upon the microprojections, wherein the solid coating includes a beneficial agent and an albumin carrier.

In another preferred embodiment of this invention, there is provided a method for delivering a beneficial agent through the stratum corneum layer of skin, the method including, providing a microprojection array having a plurality of stratum corneum-piercing microprojections, the microprojections being coated with a biocompatible coating containing a beneficial agent and a biocompatible carrier, and causing the microprojections to pierce the stratum corneum layer of a predetermined skin site, whereby the beneficial agent is released into the skin tissue.

In another preferred embodiment of this invention, there is provided an apparatus for delivering a plurality of beneficial agents to a patient, the apparatus including, a microprojection array comprising a plurality of solid coatings disposed upon the microprojections in the array. Preferably the different coatings are disposed on separate regions of the array. Each of the coatings contains a biocompatible carrier and a different beneficial agent. The microprojection array has a plurality of microprojections sized, shaped and configured to form a plurality of microslits through a stratum corneum layer when the array is applied to skin, wherein the beneficial agents are delivered into the skin tissue.

In another preferred embodiment of this invention there is provided an apparatus for delivering a plurality of beneficial agents to a patient, the apparatus including a microprojection array comprising a plurality of solid coatings disposed upon the microprojections in the array. Preferably the different coatings are disposed on separate regions of the array. Each of the coatings contains an albumin carrier and a different beneficial agent. The microprojection array has a plurality of microprojections sized, shaped and configured to form a plurality of microslits through a stratum corneum layer when the array is applied to skin, wherein the beneficial agents are delivered into the skin tissue.

In another preferred embodiment of this invention there is provided an apparatus for delivering a plurality of beneficial agents to a patient, the apparatus including a microprojection array comprising a plurality of solid coatings disposed upon the microprojections in the array. Preferably the different coatings are disposed on separate regions of the array. Each of the coatings contains a biocompatible carrier and a different beneficial agent. The microprojection array has a plurality of microprojections sized, shaped and configured to form a plurality of microslits through a stratum corneum layer when the array is applied to skin, wherein the beneficial agents are delivered into the skin tissue.

In another preferred embodiment of this invention there is provided a composition useful for forming a solid coating on microprojections in a microprojection array, the composition including a beneficial agent and a biocompatible carrier, wherein the composition is applied to the microprojections in a liquid form and forms a solid coating on the microprojection array, and wherein the solid coating allows release of the beneficial agent from the coating upon hydration of the coating.

In another preferred embodiment of this invention there is provided a composition useful for forming a solid coating on microprojections in a microprojection array, said composition comprising a beneficial agent and an albumin carrier, wherein said composition is applied to the microprojections in a liquid form and forms a solid coating on said microprojection array, and wherein the solid coating allows release of the beneficial agent from the coating upon hydration of the coating.

The coating thickness is preferably less than the thickness of the microprojections, more preferably the thickness is less than 50 micrometers and most preferably less than 25 micrometers. Generally, the coating thickness is an average thickness measured over the surfaces of the microprojections. The coating thickness can generally be increased by applying multiple coats of the coating liquid, allowing the coats to substantially dry between successive coatings.

The biocompatible carrier for coating the microprojections is selected to have sufficient adhesion characteristics and to avoid adverse interactions with the beneficial agent. The biocompatible carrier preferably also possesses good solubility properties. The most preferred biocompatible carrier is selected from the group consisting of albumin, polyglutamic acid, polyaspartic acid, polyhistidine, pentosan polysulfate, and polyamino acids. The beneficial agent must have sufficient biological activity to be effective in quantities of up to 1000 micrograms. The preferable beneficial agent is chosen from the group consisting of potent drugs, vaccines and desensitizing agents.

The coating can be applied to the microprojections using known coating methods. For example, the microprojections can be immersed into an aqueous coating solution containing the biocompatible carrier and the beneficial agent. Alternatively, the coating may be applied by spray coating and/or microfluidic dispensing techniques. More preferably, the coating may be applied using the apparatuses and methods disclosed in U.S. Patent Application Ser. No. 60/276,762 filed Mar. 16, 2001, the disclosure of which is hereby incorporated by reference in its entirety.

In another aspect of the invention, the stratum corneum piercing microprojections are formed from a sheet, preferably a metal sheet, wherein the microprojections are formed by etching or punching the sheet and then the microprojections are folded or bent out of the plane of the sheet. While the coating can be applied to the sheet before formation of the microprojections, preferably the coating is applied after the microprojections are cut or etched out but prior to being folded out of the plane of the sheet. More preferred is coating after the microprojections have been folded or bent from the plane of the sheet.

BRIEF DESCRIPTION OF THE DRAWINGS

The invention will now be described in greater detail with reference to the preferred embodiments illustrated in the accompanying drawings and figures wherein.

MODES FOR CARRYING OUT THE INVENTION

Definitions

Figure 1:
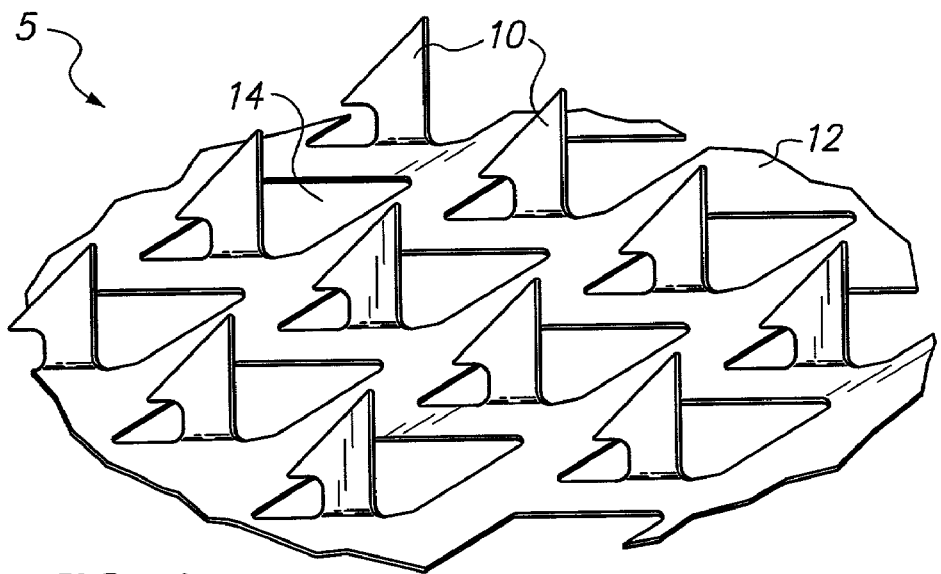
FIG. 1 is a perspective view of a portion of one example of a microprojection array.

Unless stated otherwise the following terms used herein have the following meanings.

The term "transdermal" means the delivery of an agent into and/or through the skin for local or systemic therapy.

The term "transdermal flux" means the rate of transdermal delivery.

The term "co-delivering" as used herein means that a supplemental agent(s) is/are administered transdermally either before the agent is delivered, before and during transdermal flux of the agent, during transdermal flux of the agent, during and after transdermal flux of the agent, and/or after transdermal flux of the agent. Additionally, two or more agents may be coated onto the microprojections resulting in co-delivery of the agents.

The terms "biologically active agent", and "beneficial agent" as used herein refer to an agent, such as a drug, vaccine, desensitizing agent, allergen or composition of matter or mixture containing a drug, vaccine, desensitizing agent or allergen, which is therapeutically effective when administered in an amount of less than about 1 milligram and preferably less than about 0.25 milligrams. Thus, the terms "biologically active agent", and "beneficial agent" encompass only agents that are effective at very low doses. These terms specifically include potent drugs, polypeptides, proteins, desensitizing agents, vaccines and allergens. Examples of such agents include, without limitation, polypeptide and protein drugs such as leutinizing hormone releasing hormone (LHRH), LHRH analogs (such as goserelin, leuprolide, buserelin, triptorelin, gonadorelin, and napfarelin, menotropins (urofollitropin (FSH) and LH)), vasopressin, desmopressin, corticotropin (ACTH), ACTH analogs such as ACTH (1-24), calcitonin, parathyroid hormone (PTH), vasopressin, deamino [Val4, D-Arg8] arginine vasopressin, interferon alpha, interferon beta, interferon gamma, erythropoietin (EPO), granulocyte macrophage colong stimulating factor (GM-CSF), interleukin-10 (IL-10) and glucagon; analgesic drugs such as fentanyl, sufentanil, and remifentanyl; antigens used in vaccines such as influenza vaccines, Lyme disease vaccine, rabies vaccine, measles vaccine, mumps vaccine, chicken pox vaccine, small pox vaccine and diptheria vaccine; and desensitizing agents such as cat, dust mite, dog, and pollen allergens.

The term "effective amount" or "the effective rate" refers to the amount or rate of the pharmacologically active agent needed to effect the desired, often beneficial, result. The amount of beneficial agent employed in the coating will be that amount necessary to deliver an effective amount of the beneficial agent to achieve the desired result. In practice, this will vary widely depending upon the particular beneficial agent being delivered, the site of delivery, the severity of the condition being treated, the desired effect (e.g., a pharmacological effect versus the stimulation of an immune response) and the dissolution and release kinetics for delivery of the agent from the coating into skin tissues. It is not practical to define the precise range for the effective amount of the beneficial agent incorporated into the coating on the microprojections and delivered transdermally according to the methods described herein. However, generally such agents utilized in the device of the present invention are defined as potent agents since the microprojections are sized with a limited surface area for carrying the coating. In general, the amount of the agent needed to achieve the desired therapy is less than about 1 milligram, more preferably less than about 0.25 milligram.

The term "microprojections" or "microblades" refers to the piercing elements which are adapted to pierce or cut through the stratum corneum into the underlying epidermis layer, or epidermis and dermis layers, of the skin of a living animal, particularly a human. The piercing elements should not pierce the skin to a depth that will cause significant bleeding and preferably pierce the skin to a depth which causes no bleeding. Typically the piercing elements have a blade length of less than 500 micrometers, preferably less than 250 micrometers. The microprojections typically have a width and thickness of about 5 micrometers to about 50 micrometers. The microprojections may be formed in different shapes, such as needles, hollow needles, blades, pins, punches, and combinations thereof. Furthermore, the microprojections may contain means for receiving a greater amount of coating. For example, the microprojections may contain depressions, reservoirs, grooves, or similar geometric features for retaining the coating.

The term "microprojection array" as used herein refers to a plurality of microprojections arranged in an array for piercing the stratum corneum. The microprojection array may be formed by etching or punching a plurality of microprojections from a thin sheet and folding or bending the microprojections out of the plane of the sheet to form a configuration such as that shown in FIG. 1 and in Trautman et al., U.S. Pat. No. 6,083,196. The microprojection array may also be formed in other known manners, such as by forming one or more strips having microprojections along an edge of each of the strip(s) as disclosed in Zuck, U.S. Pat. No. 6,050,988. Other microprojection arrays, and methods of making same, are disclosed in Godshall et al., U.S. Pat. No. 5,879,326 and Kamen, U.S. Pat. No. 5,983,136. The microprojection array may also be in the form of hollow needles that hold a dry pharmacologically active agent.

The term "pattern coating" refers to coating an agent onto selected areas of the microprojections. More than one agent may be pattern coated on a single microprojection array. Pattern coatings can be applied to the microprojections using known micro-fluidic dispensing techniques such as micropipetting, and ink jet printing.

The term "coating" refers to a composition including a biocompatible carrier and a beneficial agent, wherein the agent may be suspended or dissolved within the carrier. The coating is selected for its adhesion properties, its stabilization properties, its ability to be quickly dissolved within the epidermis layer, and its ability to form an amorphous glassy structure which retains soluble agents and insoluble agents when substantially dried onto the microprojections.

DETAILED DESCRIPTION

The present invention provides a device for transdermally delivering a beneficial agent to a patient in need thereof. The device has a plurality of stratum corneum-piercing microprojections extending therefrom. The microprojections are adapted to pierce through the stratum corneum into the underlying epidermis layer, or epidermis and dermis layers, but do not penetrate so deep as to cause significant bleeding. The microprojections have a substantially dry coating thereon which contains the active agent. Upon piercing the stratum corneum layer of the skin, the coating is dissolved by body fluid (intracellular fluids and extracellular fluids such as interstitial fluid) and the beneficial agent is released.

The kinetics of the coating dissolution and release will depend on many factors including the nature of the drug, the coating process, the coating thickness and the coating composition (e.g., the presence of coating formulation additives). Depending on the release kinetics profile, it may be necessary to maintain the coated microprojections in piercing relation with the skin for extended periods of time (e.g., up to about 1 hour). This can be accomplished by anchoring the microprojection array to the skin using an adhesive or by utilizing anchored microprojections such as those described in WO 97/48440, the disclosure of which is incorporated by reference in its entirety. Alternatively, the coating may be quickly dissolved, in which case the microprojection array only need be in contact with the skin for a relatively small amount of time (e.g., less than 1 minute). Still further, the microprojection array of the present invention may be deployed onto a patient's skin manually, or more preferably using an applicator such as that shown and described in U.S. Patent Application Ser. No. 60/240,307 filed Oct. 13, 2000 and Ser. No. 60/240,436 filed Oct. 13, 2000, the disclosures of which are incorporated by reference in their entirety.

Figure 5:
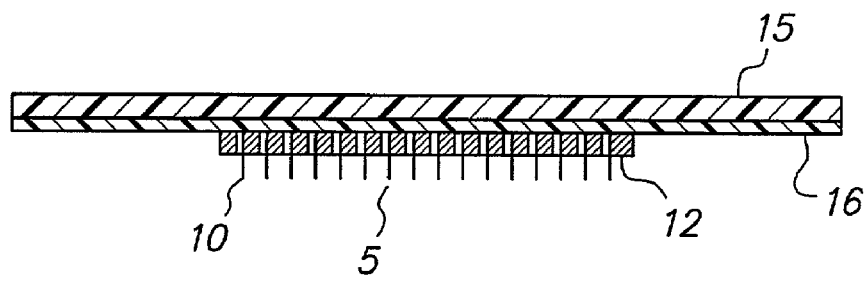
FIG. 5 is a side sectional view of a microprojection array having an adhesive backing.

FIG. 1 illustrates one embodiment of a stratum corneum-piercing microprojection array for use with the present invention. As shown in FIG. 1, a portion of the microprojection array 5 includes a plurality of microprojections 10. The microprojections 10 extend at substantially a 90 degree angle from a sheet 12 having openings 14. As shown in FIG. 5, the sheet 12 may be incorporated in a delivery patch including a backing 15 for the sheet 12. The backing 15 may further include an adhesive 16 for adhering the backing 15 and microprojection array 5 to a patient's skin. In this embodiment, the microprojections 10 are formed by either etching or punching a plurality of microprojections 10 out of a plane of the sheet 12. The microprojection array 5 may be manufactured of metals such as stainless steel, titanium, nickel titanium alloys, or similar biocompatible materials such as plastics. The microprojection array 5 is preferably constructed of titanium. Metal microprojection members are disclosed in Trautman et al., U.S. Pat. No. 6,038,196; Zuck U.S. Pat. No. 6,050,988; and Daddona et al., U.S. Pat. No. 6,091,975, the disclosures of which are herein incorporated by reference. Other microprojection members that can be used with the present invention are formed by etching silicon, by utilizing chip etching techniques or by molding plastic using etched micro-molds. Silicon and plastic microprojection members are disclosed in Godshall et al., U.S. Pat. No. 5,879,326, the disclosure of which is incorporated herein by reference.

Figure 2:
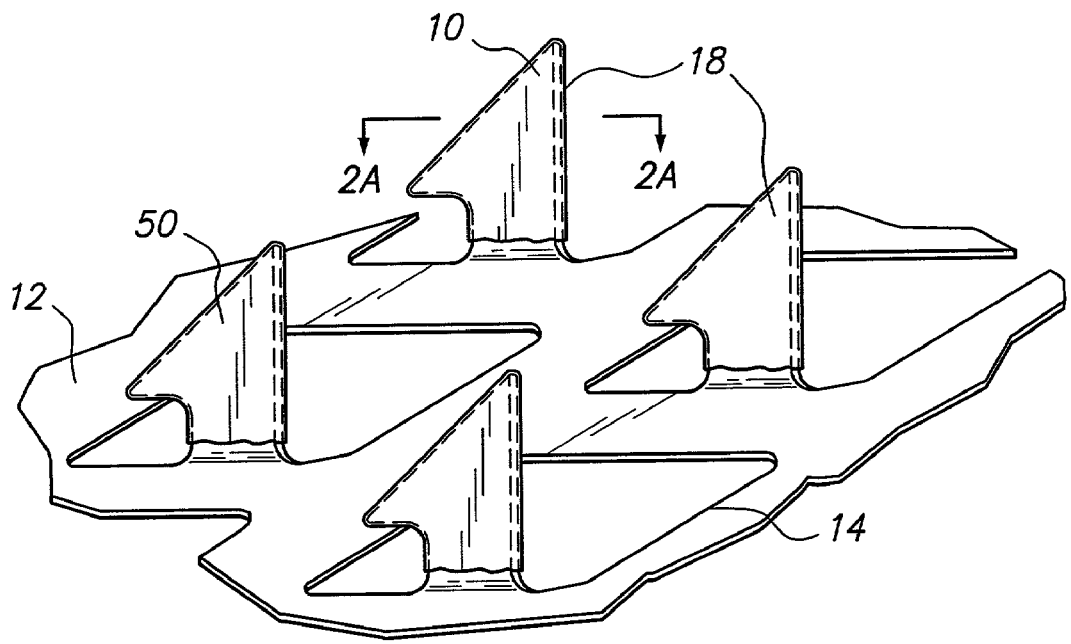
FIG. 2 is a perspective view of the microprojection array of FIG. 1 with a coating deposited onto the microprojections.

FIG. 2 illustrates the microprojection array 5 wherein the microprojections 10 have been coated with a biocompatible coating 50. The biocompatible coating 50 may partially or completely cover the microprojections 10. The biocompatible coating 50 can be applied to the microprojections before or after the microprojections are formed.

Figure 2A:
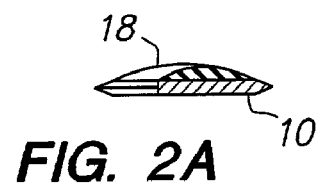
FIG. 2A is a cross sectional view of a single microprojection 10 taken along line 2A-2A in FIG. 2.

The coating 50 on the microprojections can be formed by a variety of known methods. One such method is dip-coating. Dip-coating can be described as a means to coat the microprojections by partially or totally immersing the microprojections into the beneficial agent-containing coating solution. Alternatively, the entire device can be immersed into the coating solution. In many instances, the beneficial agent within the coating may be very expensive, therefore it may be preferable to only coat the tips of the microprojections. Microprojection tip coating apparatus and methods are disclosed in Trautman et al. U.S. Patent Application Ser. No. 60/276,762 filed Mar. 16, 2001, the disclosure of which is incorporated herein by reference. As shown in the above referenced application the coating device only applies coating to the microprojections themselves and not upon the substrate/sheet that the microprojections project from. This may be desirable in the case where the cost of the beneficial agent is relatively high and therefore the coating containing the beneficial agent should only be disposed onto parts of the microprojection array that will pierce beneath the patient's stratum corneum layer. This coating technique has the added advantage of naturally forming a smooth coating that is not easily dislodged from the microprojections during skin piercing. The smooth cross section of the microprojection tip coating is more clearly shown in FIG. 2A. Other coating techniques such as microfluidic spray or printing techniques can be used to precisely deposit a coating 18 on the tips of the microprojections 10 as shown in FIG. 2. The microprojections 10 may further include means adapted to receive and/or increase the volume of the coating 18 such as apertures (not shown), grooves (not shown), surface irregularities (not shown), or similar modifications, wherein the means provides increased surface area upon which a greater amount of coating may be deposited.

Other coating methods include spraying the coating solution onto the microprojections. Spraying can encompass formation of an aerosol suspension of the coating composition. In a preferred embodiment, an aerosol suspension forming a droplet size of about 10 to about 200 picoliters is sprayed onto the microprojections and then dried.

Figure 3:
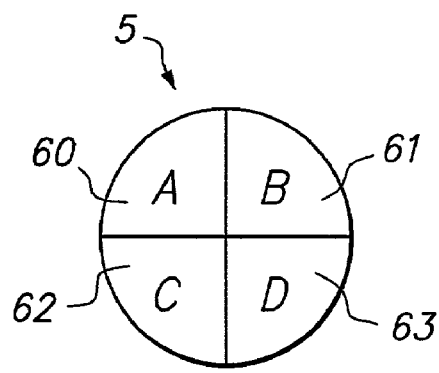
FIG. 3 is a view of a skin proximal side of a microprojection array illustrating the division of the microprojection array into various portions.
Figure 4:
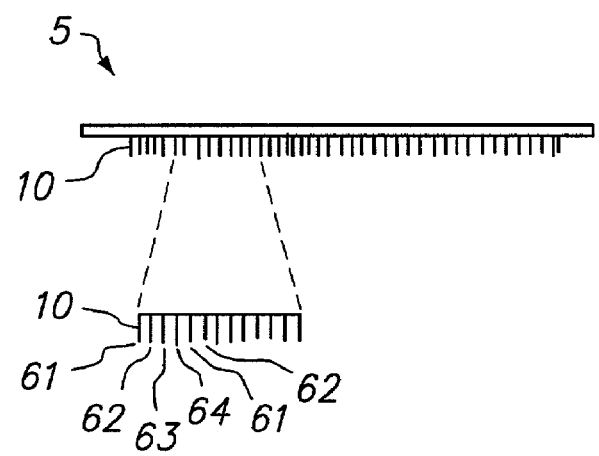
FIG. 4 is a side sectional view of a microprojection array illustrating an alternative embodiment wherein different coatings may be applied to different microprojections.

Referring now to FIGS. 3 and 4, there is shown an alternative embodiment of the present invention. As shown in FIG. 3 the microprojection array may be divided into portions illustrated at 60-63, wherein a different coating is applied to each portion, thereby allowing a single microprojection array to be utilized to deliver more than one beneficial agent during use. Referring now to FIG. 4, there is shown a cross-sectional view of a microprojection array 5, including a plurality of microprojections 10, wherein a "pattern coating" has been applied to the microprojection array 5. As shown, each of the microprojections 10 may be coated with a different biocompatible coating as indicated by reference numerals 61-64. That is, separate coatings are applied to the individual microprojections 10. The pattern coating can be applied using a dispensing system for positioning the deposited liquid onto the surface of the microprojection array. The quantity of the deposited liquid is preferably in the range of 0.1 to 20 nanoliters/microprojection. Examples of suitable precision-metered liquid dispensers are disclosed in Tisone, U.S. Pat. Nos. 5,916,524; 5,743,960; 5,741,554, and 5,738,728 the disclosures of which are incorporated herein by reference. Microprojection coating solutions can also be applied using ink jet technology using known solenoid valve dispensers, optional fluid motive means and positioning means which are generally controlled by use of an electric field. Other liquid dispensing technology from the printing industry or similar liquid dispensing technology known in the art can be used for applying the pattern coating of this invention. As shown, each of the microprojections 10 may be coated with a different biocompatible coating as indicated by reference numerals 61-64.

The liquid compositions applied to the microprojections to form the solid coatings used in the present invention are liquid compositions including a biocompatible carrier and a beneficial agent. The agent may be dissolved within the biocompatible carrier or alternatively, the agent may be suspended within the carrier. The ratio of the biocompatible carrier to the beneficial agent in the solid coating may range from about 0.2:1 weight/weight to about 5:1 weight/weight, preferably about 0.5:1 to about 2:1 weight/weight. The biocompatible carrier may be chosen from the group consisting of human albumin, bioengineered human albumin, polyglutamic acid, polyaspartic acid, polyhistidine, pentosan polysulfate, and polyamino acids. The list above is merely exemplary and should not be considered limiting in any manner, it is contemplated that other biocompatible carriers not listed may be utilized. Known adjuvants may be added to the biocompatible carrier to enhance the qualities of the coating. The biocompatible carrier is chosen such that when the coating is substantially dried it forms an amorphous glassy material. Still further, the biocompatible carrier is chosen for its adhesive properties. That is, when substantially dry, the coating is not easily dislodged from the microprojections. The coatings of the present invention allow for beneficial agents having poor aqueous stability to be retained as a solid coating on the microprojections in a stable manner. Thus a beneficial agent having poor aqueous stability may be coated onto a microprojection array wherein the microprojection array will be placed into storage for use at a latter time. Still further, the biocompatible carrier preferably exhibit good water solubility properties such that when the microprojection array is disposed within the stratum corneum and into contact with aqueous body fluids (e.g., in the epidermis) the beneficial agent is quickly delivered. Speed of beneficial agent delivery from the microprojection coating is enhanced where the solid biocompatible carrier has good water solubility. In such cases the coating is quickly dissolved upon skin piercing, thereby releasing the beneficial agent. This ability allows a physician to determine quickly if the patient is exhibiting signs of an allergic reaction to a beneficial agent particularly those in the form of a vaccine and/or antigen.

The coating thickness is dependent upon the density of the microprojections per unit area and the viscosity and concentration of the coating composition as well as the coating method chosen. In general, coating thickness must be less than 50 micrometers since thicker coatings have a tendency to slough off of the microprojections upon piercing the stratum corneum. Preferred average coating thicknesses are less that 30 micrometers as measured perpendicularly from the microprojection surface. Generally, average coating thickness is measured over the entire coated portions of the microprojection array. More preferred coating thicknesses are about 1 micrometer to about 10 micrometers.

The beneficial agents utilized with the coating are high potency agents requiring a dose of about 1 milligram or less, preferably about 0.25 milligrams or less. Amounts of the beneficial agent within this range can be coated onto the microprojection array of the type shown in FIG. 1. Such a microprojection array may have an area of up to 10 centimeters square and a microprojection density of up to 500 microprojections per centimeter squared of the sheet.

The liquid compositions used to coat the microprojections are prepared by mixing the biocompatible carrier, the beneficial agent to be delivered, and optionally any coating adjuvants, with a volatile liquid. The volatile liquid can be water, dimethyl sulfoxide, dimethyl formamide, ethanol, isopropyl alcohol, and mixtures thereof. Of these, water is most preferred. The liquid coating solution or suspension will typically have a beneficial agent concentration of about 1 to 30 wt %. The coating is dried after being deposited onto the microprojection array utilizing known drying methods such as air drying, vacuum drying, lyophilization and/or combinations thereof. It shall be understood that the term "dried" means substantially free of the volatile liquid. In the case of aqueous coating solutions or suspensions, the coatings typically retain some moisture, more typically the coatings retain a moisture content that is in equilibrium with the atmosphere surrounding the microprojection array. Thus, those skilled in the art will appreciate that a "dry" coating need not be anhydrous. Alternatively, the coating may be anhydrous, and therefore containing no water.

Other known formulation adjuvants may be added to the coating as long as they do not adversely affect the necessary solubility and viscosity characteristics of the coating and the physical integrity of the dried coating.

The coated microprojection array as described may be utilized to deliver vaccines as described above. It is also contemplated that the coated microprojections may be utilized to deliver allergens for desensitization procedures, or for allergy testing. For example, many people develop allergies to multiple allergens (i.e., dust mite, cats, dogs, pollen, etc.).

In an alternative embodiment, the biocompatible carrier may be chosen from the group consisting of sucrose, trehalose, melezitose, raffinose, stachyose. Additionally, any of the above may be added to the human albumin biocompatible carrier.

The following examples are given to enable those skilled in the art to more clearly understand and practice the present invention. They should not be considered as limiting the scope of the invention but merely as being representative thereof.

Example 1

Human Albumin Dry Film

In order to test the ability of aqueous albumin solutions to form solid coatings on titanium microprojections, a coated microprojection array was prepared in the following manner. Human albumin was utilized as a model biocompatible carrier (Sigma, Fraction V). Solutions containing 40, 20, and 10 percent by weight human albumin were prepared in sterile water. To aliquots of these solutions, fluorescein, a marker added for subsequent visualization of the dried coating, was added at a final concentration of 1 millimolar. A 1-microliter drop of this solution was spread on titanium foil having an area of about one centimeter square. The solution was allowed to dry at room temperature for about 1 hour. Fluorescence microscopy revealed that the coating, when dry, formed an amorphous glassy surface. Redissolution of the dry film in water was fast and complete.

Particle Suspension

A microprojection array having a coating containing a drug surrogate, in the form of fine particles, was prepared in the following manner. A 40 percent by weight human albumin solution was prepared in water. To 50 microliters of this solution, 50 microliters of a 20 percent by weight suspension of 0.5-micrometer fluorescent beads (i.e., the drug surrogate) was added. A 1 microliter drop of this suspension was spread on titanium foil having an area of approximately 1 square centimeter and allowed to air dry at room temperature for about 1 hour. 50 microliters of this suspension was also spread on a microprojection array and blown dry. Fluorescence microscopy demonstrated that the fluorescent beads were dispersed homogenously in the albumin matrix and that the coating of the microprojection array was effective. The coating prepared with human albumin had glasslike properties at this high particle concentration. In addition, the particles were freed readily following rehydration. A similar experiment was performed with fluorescent beads of various sizes (ranging from 0.02 to 0.5 micrometers). The final bead concentration was 20 percent by weight and the human albumin was 1 percent by weight. Similarly, microscopy revealed that the fluorescent beads are dispersed homogenously in the albumin dry coating. In each of the cases, the particles were readily freed from the dry coating following rehydration. In contrast, when a 10 percent by weight suspension of the 0.5 micrometer fluorescent beads were prepared in water and attempts were made to apply the suspension on a titanium foil, spreading was very poor and, following drying, the coating was found to be very heterogeneous.

Example 2

Cyclosporin A (CSA) Suspension

A coated microprojection array was prepared in the following manner. CSA is a water-insoluble peptide drug (1200 dalton molecular weight) used in therapeutics. 10 milligrams of CSA was dry milled. To this powder, 90 microliters of 20 percent by weight human albumin solution was added and homogenized with the CSA powder prepared in water. To this suspension, fluorescein, a marker added for subsequent visualization, was added at a final concentration of 1 millimolar. A 1 microliter drop of this suspension was spread on titanium foil having an area of 1 square centimeter and allowed to dry at room temperature for about an hour. Fluorescence microscopy demonstrated that the CSA particles were dispersed homogeneously in the albumin matrix. The CSA particles, ranging from 1 micrometer to 25 micrometers, were freed readily following rehydration.

Example 3

Soluble Drugs

A 40 percent by weight solution of human albumin was prepared in water. To 50 microliters of this solution, 50 microliters of a 40 percent by weight aqueous solution of lidocaine HCl was added. A control solution containing no albumin was also prepared. 1-microliter drops of these solutions were spread on titanium foil having an area of approximately 1 square centimeter. The solutions were allowed to air dry at room temperature for about 1 hour. An inspection revealed that the dry film of the albumin/lidocaine mixture formed a glassy amorphous surface. Redissolution of the coating in water was fast and complete. By contrast, the lidocaine solution formed a very hygroscopic film unsuitable for subsequent storage An aqueous solution containing 20 wt % human growth hormone (20 wt % hGH), and 20 wt % sucrose was prepared. Microprojection arrays (microprojection length 250 µm, 595 microprojections per array) had a skin contact area 2 cm². The tips of the microprojections were coated with this solution by passing the arrays over a rotating drum carrying the hGH/sucrose solution using the method and apparatus disclosed in U.S. Patent Application Ser. No. 60/276,762 filed Mar. 16, 2001. Four successive coatings were performed on each microprojection array at 4° C. The amount of protein coated on the arrays was evaluated by total protein assay. An average of 9.5±0.9 µg of hGH was coated per array. Scanning electron microscopy revealed good uniformity of coating from microprojection to microprojection, with the coating limited to the first 100 µm of the microprojection tip. On the microprojection itself, the coating was found unevenly distributed. Most of the solid coating appeared to be located in caps centered on the geometric center of the faces of the coated area of the microprojections. Following two days storage in a vacuum chamber, the solid coating presented a very smooth surface with absence of cracking and it was demonstrated to adhere very tightly to the microprojections. The maximum measured thickness of the coating was about 4 µm while the average calculated thickness over the entire coated area was only about 1.7 µm. Overall, the coating presented good aerodynamics and good adhesion, consistent with minimum effect on penetration of the microprojections into the skin and minimal removal of the drug from the microprojection during penetration.

Some of the hGH tip-coated arrays were subsequently used for drug delivery studies in hairless guinea pigs. The application of the coated microprojection arrays was done using an impact applicator (total energy=0.4 Joules, delivered in less than 10 milliseconds) using a spring-driven impact applicator or the type disclosed in U.S. Patent Application Ser. No. 60/240,307 filed Oct. 13, 2000. The arrays were left on the skin after application for 5 seconds, 5 minutes, or 1 hour, in groups of three animals. Blood was collected at time intervals for plasma hGH determination by ELISA. The results showed that hGH delivery was the same at all wearing times. On average, 5 µg of hGH was delivered in each animal, which accounts for approximately 50% of the coated dose. Assuming that the bioavailability from microprojection delivery was similar to that of subcutaneous administration (65%), about 80% of the coated dose was delivered into the skin. In addition, as compared to subcutaneous injection, a quicker onset was observed following microprojection administration (tmax of 60 minutes and 30 minutes, respectively; Cmax of 5 ng/mL and 13 ng/mL, respectively). Finally, the 5 minute wearing time group had the smallest CV (30%), which is even smaller than that observed following subcutaneous injection (50%).

The invention claimed is:

1. A device for delivering a beneficial agent through the stratum corneum, the device comprising:
   a plurality of stratum corneum-piercing microprojections;
   a coating disposed as a homogenous, amorphous glassy form upon at least a portion of said microprojections, wherein the coating is substantially dried and includes at least one beneficial agent and at least one water soluble biocompatible carrier;
   wherein said agent is dissolved or suspended in said carrier, wherein said coating is placed in contact with body fluid after the microprojections have pierced the stratum corneum, and wherein said at least one water soluble biocompatible carrier comprises human albumin.

2. The device of claim 1, wherein said human albumin is bio-engineered human albumin.

3. The device of claim 1, wherein the at least one beneficial agent is suspended in the at least one water soluble biocompatible carrier.

4. The device of claim 1, wherein the at least one beneficial agent is selected from the group consisting of vaccines and desensitizing agents.

5. The device of claim 1, wherein the ratio of all biocompatible carriers to all beneficial agents range from about 0.2:1 to about 5:1 weight/weight.

6. The device of claim 1, wherein the ratio of all biocompatible carriers to all beneficial agents range from about 0.5:1 to about 2:1 weight/weight.

7. The device of claim 1, wherein the coating includes a plurality of beneficial agents.

8. The device of claim 1, wherein each of the at least one beneficial agents are included on coatings which are on separate portions of the plurality of microprojections.

9. The device of claim 1, wherein the at least one biocompatible carrier further includes at least one carrier selected from the group consisting of sucrose, trehalose, melezitose, raffinose, and stachyose.

10. A device for delivering a beneficial agent through the stratum corneum, the device comprising:
    a plurality of stratum corneum-piercing microprojections;
    a coating disposed as a homogeneous, amorphous glassy form upon at least a portion of said microprojections;
    wherein the coating is substantially dried and includes at least one beneficial agent and at least one water soluble biocompatible carrier;
    wherein said agent is dissolved or suspended in said carrier, wherein said coating is placed in contact with body fluid after the microprojections have pierced the stratum corneum, and wherein the at least one water soluble biocompatible carrier is selected from the group consisting of dextran sulfate, pentosan polysulfate, polyglutamic acid, polyaspartic acid, polyhistidine, and non-reducing sugars.

11. A device for delivering a beneficial agent through the stratum corneum, the device comprising:
    a plurality of stratum corneum-piercing microprojections;
    a coating disposed as a homogeneous, amorphous glassy form upon at least a portion of said microprojections;
    wherein the coating is substantially dried and includes at least one beneficial agent and at least one water soluble biocompatible carrier;
    wherein said agent is dissolved or suspended in said carrier, wherein said coating is placed in contact with body fluid after the microprojections have pierced the stratum corneum, and wherein the at least one water soluble biocompatible carrier is a polyamino acid.

* * * * *